(12) United States Patent
Nagano et al.

(10) Patent No.: US 8,382,673 B2
(45) Date of Patent: Feb. 26, 2013

(54) ULTRASONIC ENDOSCOPE

(75) Inventors: Kazuhiko Nagano, Ashigarakami-gun (JP); Atsushi Osawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 874 days.

(21) Appl. No.: 12/190,080

(22) Filed: Aug. 12, 2008

(65) Prior Publication Data
US 2009/0088646 A1  Apr. 2, 2009

(30) Foreign Application Priority Data

Sep. 28, 2007  (JP) .................................. 2007-254952

(51) Int. Cl.
*A61B 8/00* (2006.01)
(52) U.S. Cl. ........................................ 600/462; 600/459
(58) Field of Classification Search .................. 600/459, 600/462
See application file for complete search history.

(56) References Cited

U.S. PATENT DOCUMENTS 7,922,651 B2 *  4/2011  Yamada et al. ............... 600/104
2007/0016064 A1 *  1/2007  Yamashita et al. ........... 600/459

FOREIGN PATENT DOCUMENTS

| JP | 59164045 A | 9/1984 |
|---|---|---|
| JP | 6173639 A | 4/1986 |
| JP | 63-242246 A | 10/1988 |
| JP | 852138 A | 2/1996 |
| JP | 09075345 A | 3/1997 |
| JP | 09-140706 A | 6/1997 |
| JP | 3061292 U | 6/1999 |
| JP | 2006158483 A | 6/2006 |
| JP | 2006-204552 A | 8/2006 |

OTHER PUBLICATIONS

Japanese Office Action corresponding to Japanese Patent Application No. 2007-254952, dated Dec. 13, 2011.
Japanese Office Action corresponding to Japanese Patent Application No. 2007-254952, dated Nov. 27, 2012.

* cited by examiner

*Primary Examiner* — Peter Luong
(74) *Attorney, Agent, or Firm* — Sughrue Mion, PLLC

(57) ABSTRACT

An ultrasonic endoscope in which the temperature rise can be suppressed with a reduced diameter. The ultrasonic endoscope includes: an ultrasonic transducer part including plural ultrasonic transducers; an exterior member for accommodating the ultrasonic transducer part; and a heat conducting part provided inside of the exterior member and respectively connected to the ultrasonic transducer part and an inner surface of the exterior member. It is preferable that the heat conducting part has a coefficient of thermal conductivity equal to or more than 10 W/(m·K). Further, it is preferable that one of the heat conducting member and the exterior member has an electric insulation property.

8 Claims, 12 Drawing Sheets

102

ULTRASONIC ENDOSCOPE

BACKGROUND OF THE INVENTION

1. Field of the Invention

The present invention relates to an ultrasonic endoscope to be used for body cavity examination of upper digestive organs, bronchial tube, and so on.

2. Description of a Related Art

In medical fields, various imaging technologies have been developed in order to observe the interior of an object to be inspected and make diagnoses. Among them, especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in the obstetrics, but also gynecology, circulatory system, digestive system, and so on.

The ultrasonic imaging is an image generation technology utilizing the nature of ultrasonic waves that the waves are reflected at a boundary between regions having different acoustic impedances (e.g., a boundary between structures) Typically, an ultrasonic diagnostic apparatus using ultrasonic imaging is provided with a body surface ultrasonic probe to be used in contact with the object or intracavity ultrasonic probe to be used by being inserted into a body cavity of the object. Further, in recent years, an ultrasonic endoscope in combination of an endoscope for optically observing the interior of the object and an ultrasonic probe for intracavity has been used.

Ultrasonic beams are transmitted toward the object such as a human body and ultrasonic echoes generated in the object are received by using the ultrasonic endoscope, and thereby, ultrasonic image information is acquired. On the basis of the ultrasonic image information, ultrasonic images of structures (e.g., internal organs, diseased tissues, or the like) existing within the object are displayed on a display unit of an ultrasonic endoscopic apparatus main body connected to the ultrasonic endoscope.

As an ultrasonic transducer for transmitting and receiving ultrasonic waves, a vibrator (piezoelectric vibrator) having electrodes formed on both sides of a material that expresses a piezoelectric property (a piezoelectric material) is generally used. When a voltage is applied to the electrodes of the vibrator, the piezoelectric material expands and contracts due to the piezoelectric effect and generates ultrasonic waves. Accordingly, plural vibrators are one-dimensionally or two-dimensionally arranged and the vibrators are sequentially driven, and thereby, an ultrasonic beam to be transmitted in a desired direction can be formed. Further, the vibrators expand and contract by receiving propagating ultrasonic waves and generate electric signals. These electric signals are used as reception signals of the ultrasonic waves.

When ultrasonic waves are transmitted, drive signals having great energy are supplied to the ultrasonic transducers. In this regard, not the entire energy of the drive signals is converted into acoustic energy but a significant proportion of the energy becomes heat, and there has been a problem that the temperature rises in use of the ultrasonic endoscope. However, the insertion part of the ultrasonic endoscope is used in direct contact with the living body such as a human body, and a request that the surface temperature of the insertion part of the ultrasonic endoscope is controlled to a predetermined temperature or less has been made for safety reasons of low-temperature burn and so on.

As a related technology, Japanese Patent Application Publication JP-A-9-140706 discloses a technology of collecting heat generated from a heat source within a probe by using heat collecting means and guiding the heat collected by the heat collecting means to a location apart from the heat source by using heat transfer means such as a heat pipe. However, the outer diameter of the ultrasonic probe needs to be smaller when the ultrasonic probe is inserted into a human body, while the diameter of the heat transfer means needs to be larger for sufficiently high heat transfer coefficient of the heat transfer means. Accordingly, it is difficult to apply the technology of JP-A-9-140706 to an ultrasonic endoscope to be inserted into a human body.

Japanese Patent Application Publication JP-P2006-204552A discloses a technology of cooling a vibrator part by transferring the heat generated in the vibrator part and a circuit board to a shield case via a heat conducting part, and allowing a heat absorbing part including a refrigerant feeder and a refrigerant pipe to absorb the heat transferred to the shield case. However, when the ultrasonic probe is inserted into a human body, the outer diameter of the ultrasonic probe needs to be smaller, and it is difficult to apply the technology of JP-P2006-204552A to an ultrasonic endoscope to be inserted into a human body.

Japanese Registered Utility Model JP-Z-3061292 discloses that a heat transfer structure is provided in contact with an integrated circuit within an ultrasonic transducer, for extracting heat generated there to the outside, and the heat extracted by the heat transfer structure is transferred to an electrically conducting material that functions as a heat sink within a communication cable. However, in an ultrasonic endoscope, the signal cable has a small sectional area, and, in the case where the signal cable is used for heat dissipation, no sufficient heat dissipation effect is obtained due to the small sectional area.

Japanese Patent Application Publication JP-A-63-242246 discloses an ultrasonic probe having a force-feed cooling member mounted on the leading end of a head case. In the ultrasonic probe, a cooling pipe is provided in the force-feed cooling member, and an ultrasonic transducer part is cooled by a cooling medium (e.g., water) flowing through the cooling pipe. However, the outer diameter of the ultrasonic probe becomes larger when the cooling pipe is provided.

As described above, in the conventional ultrasonic probe structures, the outer diameter of the ultrasonic probe becomes larger when attempting to reduce the temperature rise of the ultrasonic probe. Accordingly, development of a new heat dissipation structure is desired in an ultrasonic endoscope.

SUMMARY OF THE INVENTION

The present invention has been achieved in view of the above-mentioned problems. A purpose of the present invention is to provide an ultrasonic endoscope having a new heat dissipation structure.

In order to accomplish the purpose, an ultrasonic endoscope according to one aspect of the present invention includes: an ultrasonic transducer part including plural ultrasonic transducers; an exterior member for accommodating the ultrasonic transducer part; and a heat conducting part provided inside of the exterior member and respectively connected to the ultrasonic transducer part and an inner surface of the exterior member.

According to the present invention, the heat generated in the ultrasonic transducer part transfers to the exterior member via the heat conducting part, and released to the outside from the surface of the exterior member. Therefore, a new heat dissipation structure can be provided by which the heat dissipation of the heat generated in the ultrasonic transducer part from the surface of the exterior member is promoted.

DESCRIPTION OF THE PREFERRED EMBODIMENTS

Hereinafter, embodiments of the present invention will be explained in detail with reference to the drawings. The same reference numbers will be assigned to the same component elements and the description thereof will be omitted.

Figure 1:
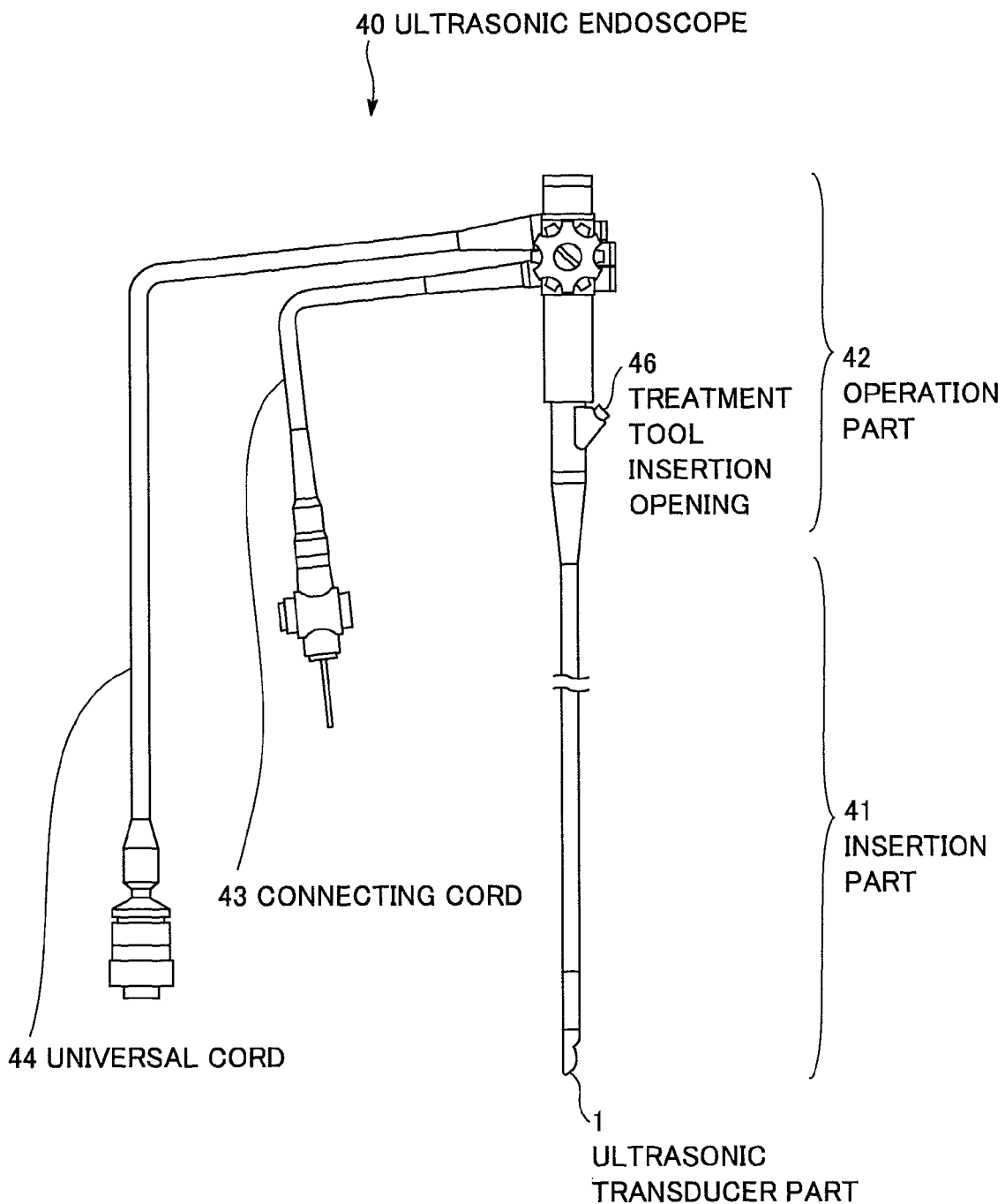
FIG. 1 is a schematic diagram showing an appearance of an ultrasonic endoscope according to the respective embodiments of the present invention.

FIG. 1 is a schematic diagram showing an appearance of an ultrasonic endoscope according to the respective embodiments of the present invention. As shown in FIG. 1, an ultrasonic endoscope 40 includes an insertion part 41, an operation part 42, a connecting cord 43, and a universal cord 44. The insertion part 41 includes an elongated tube formed of a member having flexibility for insertion into the body (e.g., into the bronchial tube) of an object to be inspected, and an ultrasonic transducer part 1 at the leading end thereof.

The operation part 42 is provided at the base end of the insertion part 41, and connected to an ultrasonic endoscopic apparatus main body (not shown) via the connecting cord 43 and the universal cord 44. A treatment tool insertion opening 46 provided in the operation part 42 is a hole for leading in a treatment tool such as a punctuation needle or forceps. Various treatments are performed within a body cavity of an object to be inspected by operating it at the operation part 42.

Figure 2:
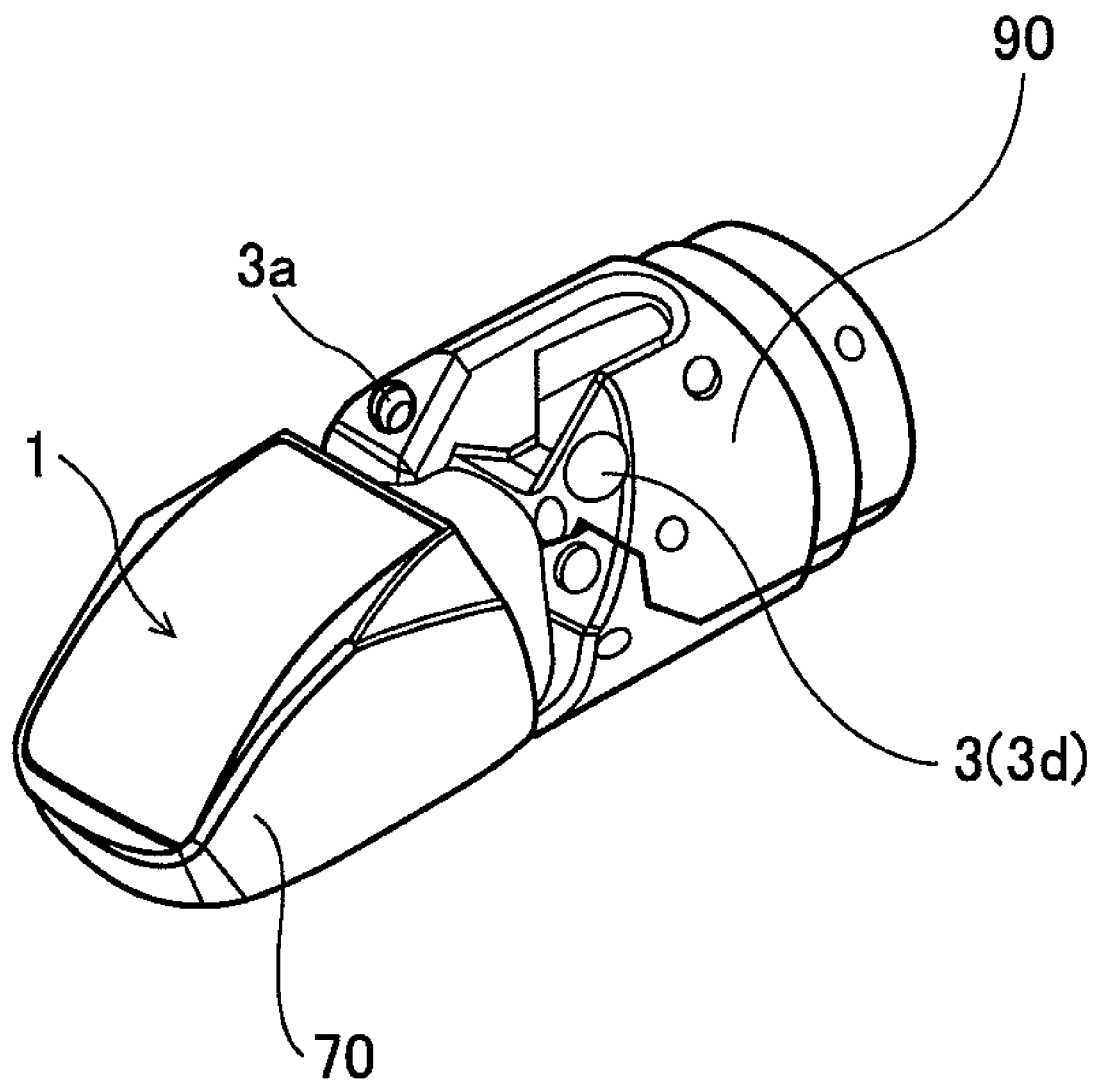
FIG. 2 is a perspective view showing a leading end of an insertion part of the ultrasonic endoscope according to the first embodiment.
Figure 3:
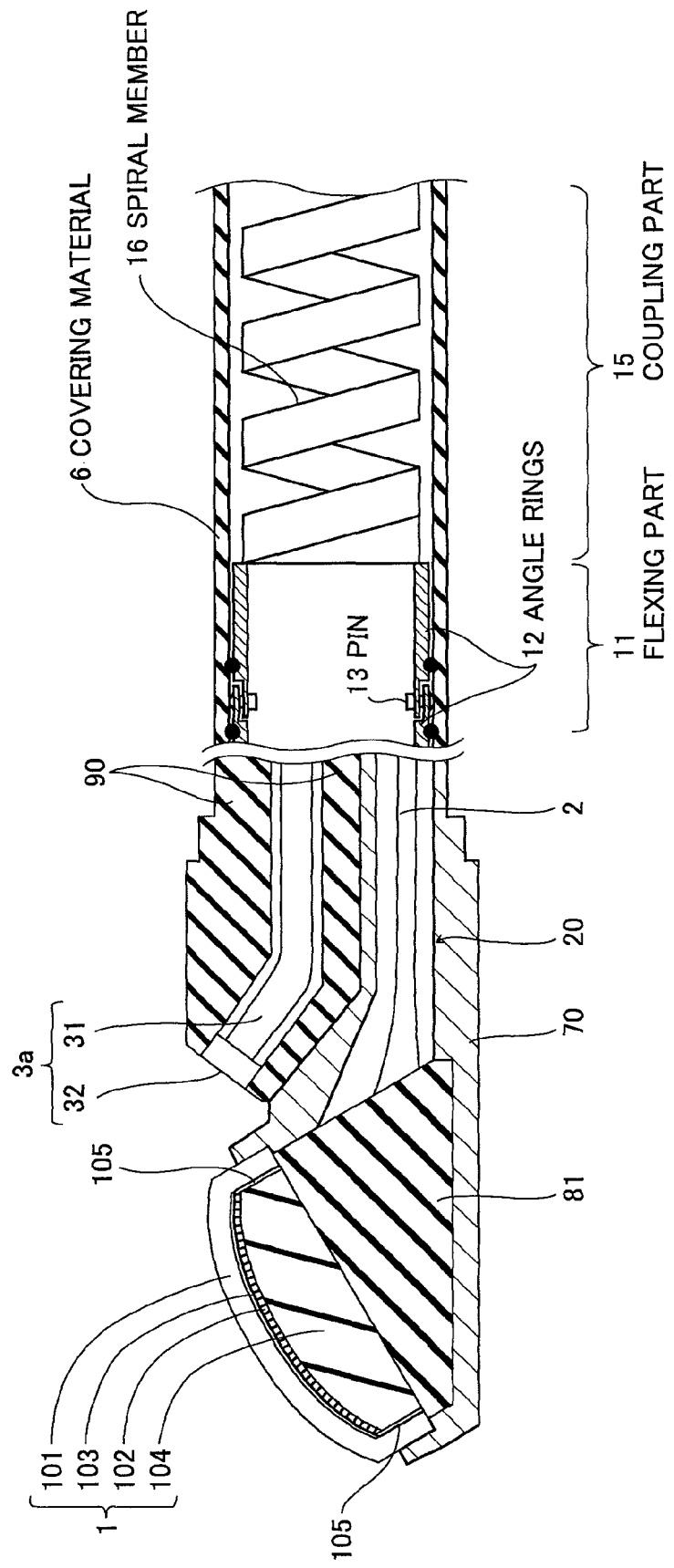
FIG. 3 is a sectional view showing a structure of a leading end of an insertion part of the ultrasonic endoscope according to the first embodiment.

FIG. 2 is a perspective view showing the leading end of the insertion part of the ultrasonic endoscope according to the first embodiment of the present invention. FIG. 3 is a sectional view showing a structure of the leading end of the insertion part of the ultrasonic endoscope according to the first embodiment. As shown in the drawings, the leading end of the insertion part of the ultrasonic endoscope according to the embodiment has an ultrasonic transducer part 1 for transmitting and receiving ultrasonic waves, signal lines 2 for transmitting signals between the ultrasonic transducer part 1 and the ultrasonic endoscopic apparatus main body, a light guide part 3a for applying light to an affected part, an imaging part 3 (shown in FIG. 2) for optically imaging the affected part, an exterior member 70 for accommodating the ultrasonic transducer part 1 and the leading end of the signal lines 2, an optics holding member 90 attached to the exterior member 70, for holding the imaging part 3 and the light guide part 3a, a flexing part 11 flexible for supporting the exterior member 70 and the optics holding member 90, a coupling part 15 for coupling the flexing part 11 to the operation part 42 (shown in FIG. 1), and a covering material 6 for covering at least the flexing part 11 and the coupling part 15. The outer diameter of the leading end is 6.9 mm or less, for example. The exterior member 70 is formed of stainless steel such as SUS 304, for example, and the optics holding member 90 is formed of a resin such as polyetherimide.

The imaging part 3 has an observation window 3d provided in the optics holding member 90, an objective lens fit in the observation window 3d, and an input end of a solid-state image sensor such as a CCD camera or an image guide provided in the imaging position of the objective lens. The light guide part 3a has an illumination window 32 provided in the optics holding member 90 and an optical fiber 31 for outputting light from the illumination window 32. An illumination lens is fit in the illumination window 32.

The flexing part 11 is configured by arranging supporting points for bending of plural top-like angle rings 12 with displacement of 90° with respect to each other in a staggered manner. The top-like angle rings 12 are connected to one another by pins 13 such that the top-like angle rings 12 can be relatively displaced, thereby form a hinge structure. The coupling part 15 includes a spiral member 16. The spiral member 16 is formed of stainless steel, for example. The covering material 6 is formed of an electrically insulating material of fluorine-containing rubber, for example.

The ultrasonic transducer part 1 is a convex-type multirow array, for example, and slantwise provided on the upper part of the leading end of the exterior member 70. The ultrasonic transducer part 1 has plural ultrasonic transducers 102 provided on the upper face of a backing material 104, and an acoustic lens 101 covering the plural ultrasonic transducers 102, for example. One or some acoustic matching layers 103 are provided between the acoustic lens 101 and the ultrasonic transducers 102. The plural ultrasonic transducers 102 are arranged in five rows, for example.

The acoustic matching layer 103 is formed of Pyrex (registered trademark) glass or an epoxy resin containing metal powder, which easily propagates ultrasonic waves, for providing matching of acoustic impedances between the object as a living body and the ultrasonic transducers 102. Thereby, the ultrasonic waves transmitted from the ultrasonic transducers 102 efficiently propagate within the object.

The acoustic lens 101 is formed of silicone rubber, for example, and exposed from the upper surface of the exterior member 70. The acoustic lens 101 focuses an ultrasonic beam, which has been transmitted from the ultrasonic transducers 102 and propagates through the acoustic matching layer 103, at a predetermined depth within the object.

The backing material 104 is formed of an elastomer such as rubber, for example, or may include mixture of a base material formed of an elastomer and a filler having higher heat conductivity than the base material. In this case, as the filler, ferrite, tungsten, alumina, or the like is used. The ultrasonic transducer part 1 is housed within the exterior member 70 with the acoustic lens 101 exposed. Since the ultrasonic waves generated by the ultrasonic transducers 102 are also applied to the backing material 104, heat is also generated from the backing material 104.

A heat conducting member 81 is connected to the back face of the backing material 104. The heat conducting member 81 is located inside the exterior member 70 and under the ultrasonic transducer part 1. It is preferable that the heat conducting member 81 is connected to the entire surface of the back face of the backing material 104, but may be connected to a part (e.g., more than a half of the back face) thereof. Further, the heat conducting member 81 is also connected to a part of the inner surface of the exterior member 70, e.g., the part opposite to the backing material 104. It is preferable that the heat conducting member 81 is in contact with the inner surface of the exterior member 70 in a wide area. The heat conducting member 81 is formed of an electrically insulating material having a coefficient of thermal conductivity equal to or more than 2 W/(m·K) such as aluminum nitride (AlN), for example. The coefficient of thermal conductivity of the heat conducting member 81 is preferably equal to or more than 10 W/(m·K). The heat conducting member 81 and the backing material 104 are connected to each other via an adhesive having high thermal conductivity, for example, and the heat conducting member 81 and the inner surface of the exterior member 70 are connected to each other via the adhesive, for example.

The signal lines 2 include plural shield lines, for example, and extend to the side face of the backing material 104 around the heat conducting member 81. The signal lines 2 pass through a signal line holding part 20. The plural shield lines are respectively connected to electrode pads on one or two FPCs (flexible printed circuits) 15 provided on one or two side faces of the backing material 104, and respectively connected to the plural ultrasonic transducers 102 via the electrode pads and wiring patterns formed within FPCs 105.

In the above-mentioned configuration, the heat generated in the ultrasonic transducers 102 transfers to the heat conducting member 81 via the backing material 104, and the heat generated in the backing material 104 transfers to the heat conducting member 81. The heat that has transferred to the heat conducting member 81 transfers to the exterior member 70 and is released to the outside from the exterior member 70. Therefore, the heat staying in the ultrasonic transducer part 1 is suppressed, and consequently, the temperature rise at the leading end of the insertion part of the ultrasonic endoscope 40 can be suppressed. In the case where the filler having high heat conductivity is mixed in the backing material 104, the effect becomes especially great. Further, since the heat conducting member 81 and the exterior member 70 are formed of insulating materials, the electric insulation of the ultrasonic transducer part 1 from the outside can be ensured.

Figure 11:
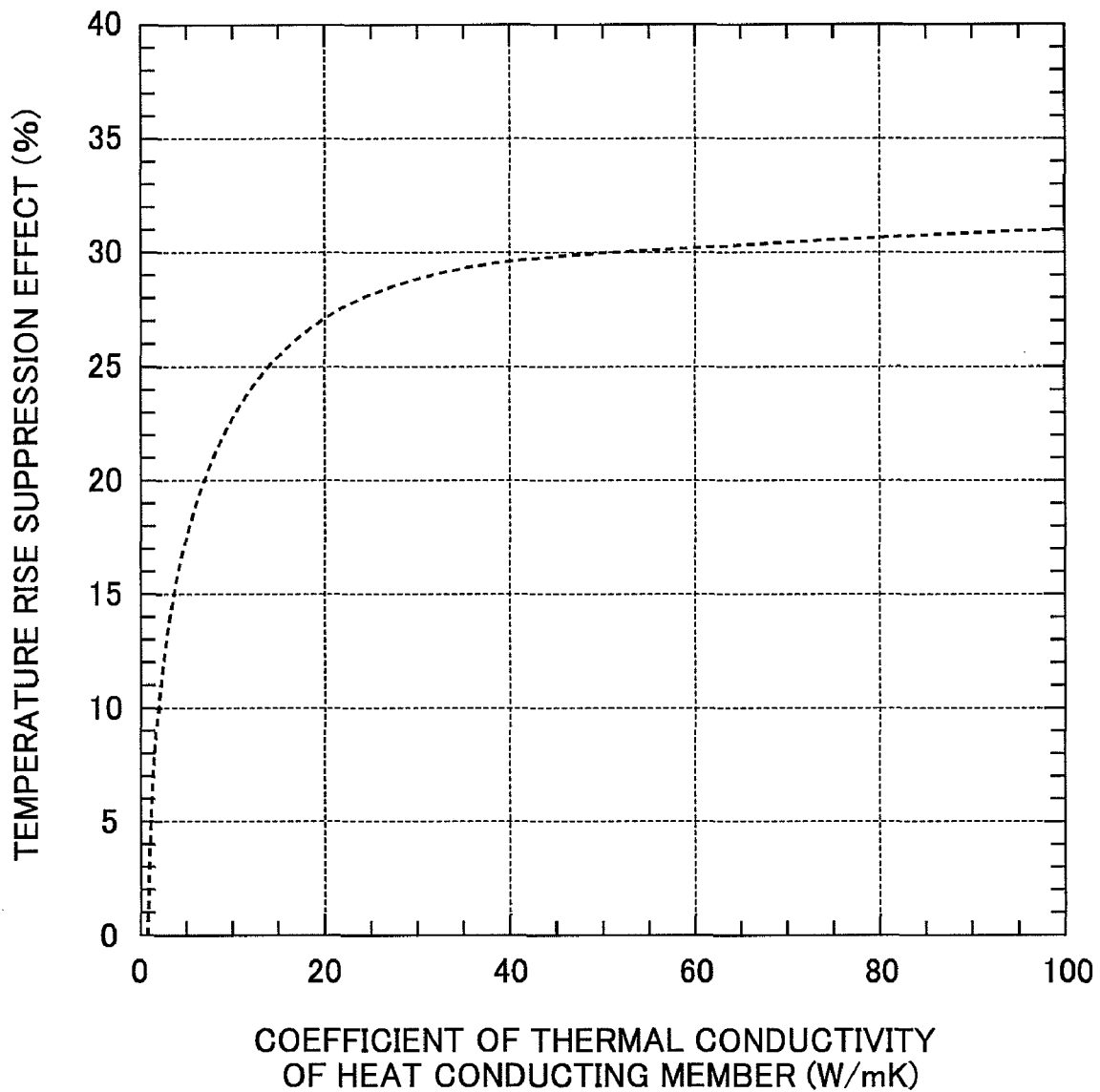
FIG. 11 is a graph showing a simulation result of a coefficient of thermal conductivity and a temperature rise suppression effect of a heat conducting member in the first embodiment.

FIG. 11 shows a simulation result of the coefficient of thermal conductivity and the temperature rise suppression effect of the heat conducting member 81 in the structure shown in the embodiment. As shown in FIG. 11, in comparison to the structure in which electrodes are provided on the lower face of the backing material, in the structure shown in the embodiment, the temperature rise of the surface of the acoustic lens 101 can be reduced by about 15% when the coefficient of thermal conductivity of the heat conducting member 81 is 2.5 W/mK, and the temperature rise of the surface of the acoustic lens 101 can be reduced by about 24% when the coefficient of thermal conductivity of the heat conducting member 81 is 10 W/mK.

Further, it is not necessary to increase the diameter of the leading end of the insertion part of the ultrasonic endoscope for providing the heat conducting member 81. Therefore, the diameter of the leading end of the insertion part of the ultrasonic endoscope 40 is not increased.

Figure 4:
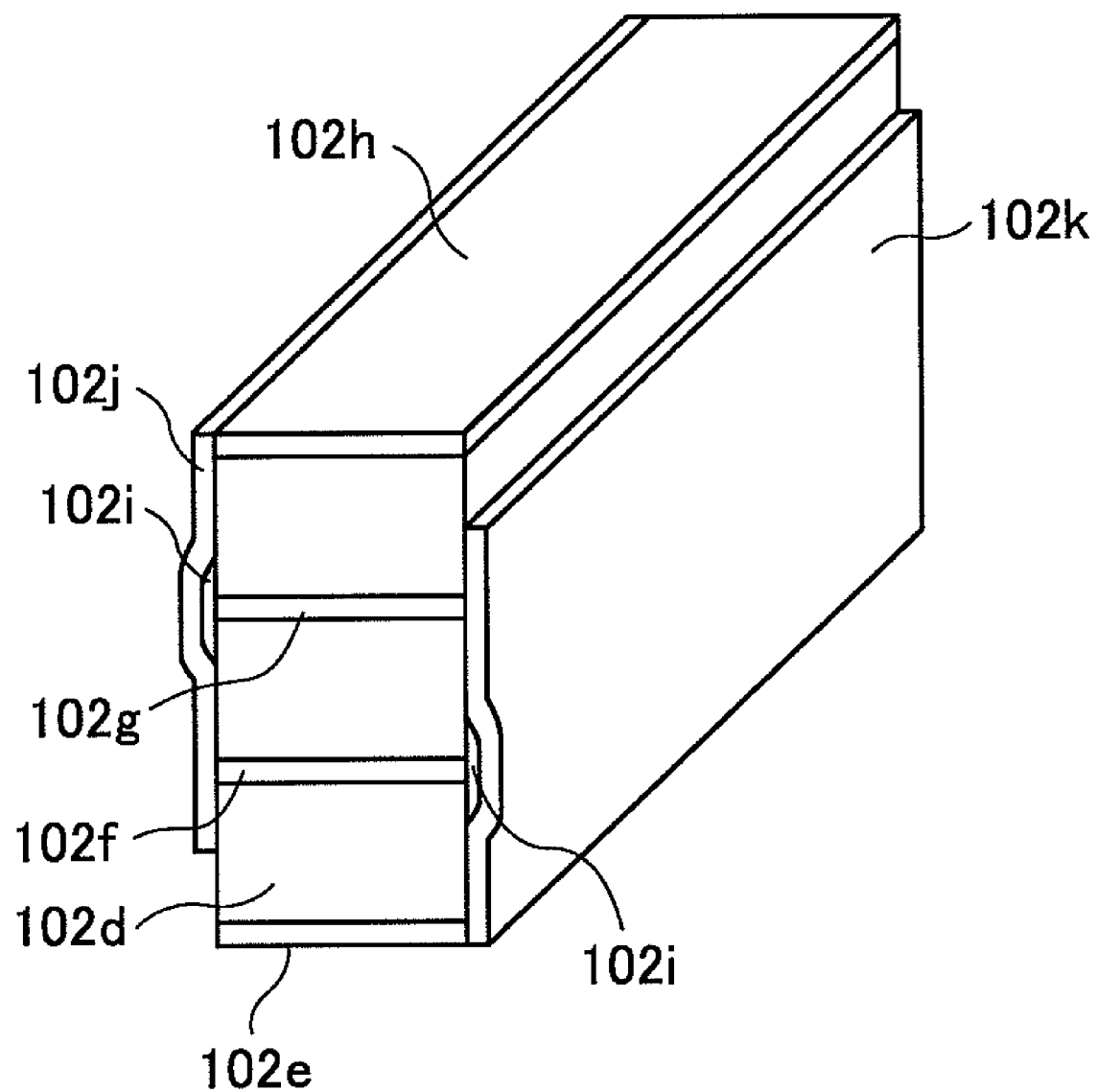
FIG. 4 is a perspective view for explanation of a configuration of an ultrasonic transducer.

FIG. 4 is a perspective view for explanation of the configuration of the ultrasonic transducer 102. The ultrasonic transducer 102 includes plural piezoelectric material layers 102$d$ formed of PZT or the like, a lower electrode layer 102$e$, internal electrode layers 102$f$ and 102$g$ alternately inserted between the plural piezoelectric material layers 102$d$, an upper electrode layer 102$h$, insulating films 102$i$, and side electrodes 102$j$ and 102$k$.

The lower electrode layer 102$e$ is connected to the side electrode 102$k$ at the right side in the drawing and insulated from the side electrode 102$j$ at the left side in the drawing. The upper electrode layer 102$h$ is connected to the side electrode 102$j$ and insulated from the side electrode 102$k$. Further, the internal electrode layer 102$f$ is connected to the side electrode 102$j$ and insulated from the side electrode 102$k$ by the insulating film 102$i$. On the other hand, the internal electrode layer 102$g$ is connected to the side electrode 102$k$ and insulated from the side electrode 102$j$ by the insulating film 102$i$. The plural electrodes of the ultrasonic transducer 102 are formed in this fashion, three pairs of electrodes for applying electric fields to the three layers of piezoelectric material layers 102$d$ are connected in parallel. The number of piezoelectric material layers is not limited to three, but may be two or four or more.

In the multilayered ultrasonic transducer 102, the area of electrodes in contact with the piezoelectric material layers 102$d$ is larger than that of a single-layered element, and the electric impedance is lower. Therefore, the multilayered ultrasonic transducer has increased vibration output and operates more efficiently for the applied voltage than the single-layered piezoelectric vibrator having the same size. Specifically, given that the number of piezoelectric material layers 102$d$ is N, the number of the piezoelectric material layers is N-times that of the single-layered piezoelectric vibrator and the thickness of each piezoelectric material layer is 1/N of that of the single-layered piezoelectric vibrator, and the electric impedance of the ultrasonic transducer 102 is $1/N^2$-times that of the single-layered piezoelectric vibrator. Therefore, the electric impedance of ultrasonic transducer 102 can be adjusted by increasing or decreasing the number of stacked piezoelectric material layers 102$d$, and thus, the electric impedance matching between a drive circuit or a preamplifier and itself is easily provided, and the sensitivity can be improved.

On the other hand, the capacitance is increased due to the stacked form of the ultrasonic transducer 102, and the amount of heat generated from the ultrasonic transducer 102 becomes larger. However, since the heat conducting member 81 is provided in the embodiment, the heat generated in the ultrasonic transducers 102 is efficiently released to the outside via the exterior member 70, and consequently, the temperature rise at the leading end of the insertion part of the ultrasonic endoscope 40 can be suppressed.

Figure 5:
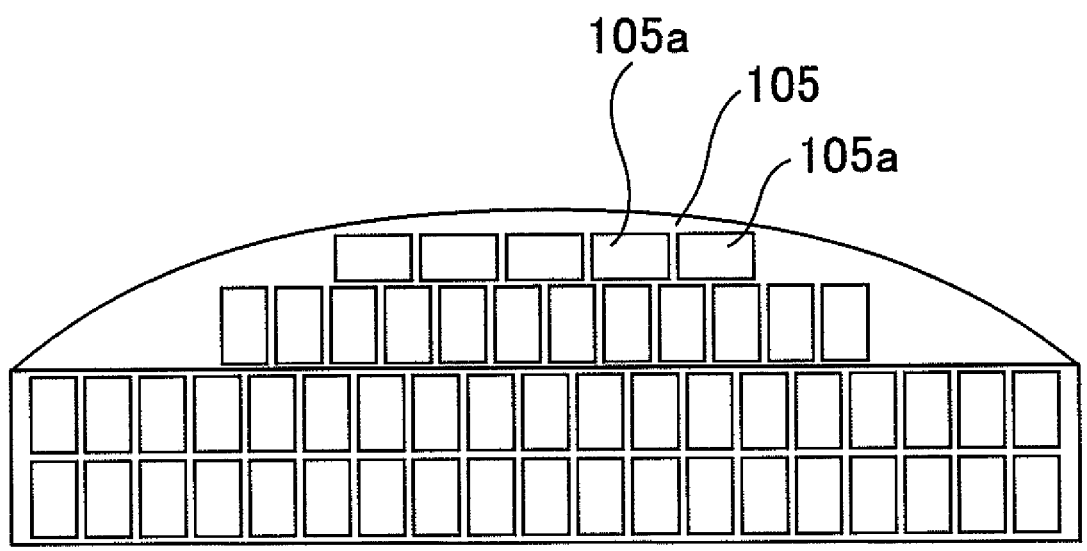
FIG. 5 is a plan view for explanation of a configuration of an FPC.

FIG. 5 is a plan view for explanation of a configuration of the FPC 105. The FPC 105 shown in the drawing is attached to the side face nearly in parallel to the section shown in FIG. 3 of the side faces of the backing material 104. As described above, the FPC 105 is provided on the side face of the backing material 104, and connects the shield lines of the signal lines 2 to the ultrasonic transducers 102. Plural electrode pads 105*a* are arranged along the side face of the backing material 104 and connected to the shield lines of the signal lines 2. Because of the arrangement, there is no need to provide the FPC 105 on the back face of the backing material 104, and the back face of the backing material 104 can be connected to the heat conducting member 81. Part of the FPC 105 may extend from the side face to the periphery of the back face of the backing material 104. In this case, the electrode pads 105*a* are also provided on the part of the FPC 105 located at the periphery. Further, the heat conducting member 81 is connected to the back face of the backing material 104 in a position where the heat conducting member 81 and the FPC 105 do not overlap.

As described above, according to the first embodiment of the present invention, the heat generated in the ultrasonic transducers 102 transfers to the heat conducting member 81 via the backing material 104. The heat that has transferred to the heat conducting member 81 transfers to the exterior member 70 and is released to the outside from the exterior member 70. Therefore, the temperature rise at the leading end of the insertion part of the ultrasonic endoscope 40 can be suppressed. Further, since the exterior member 70 is formed of an electrically insulating material, the electric insulation of the outer surface of the exterior member 70 from the ultrasonic transducer part 1 can be ensured.

Figure 6:
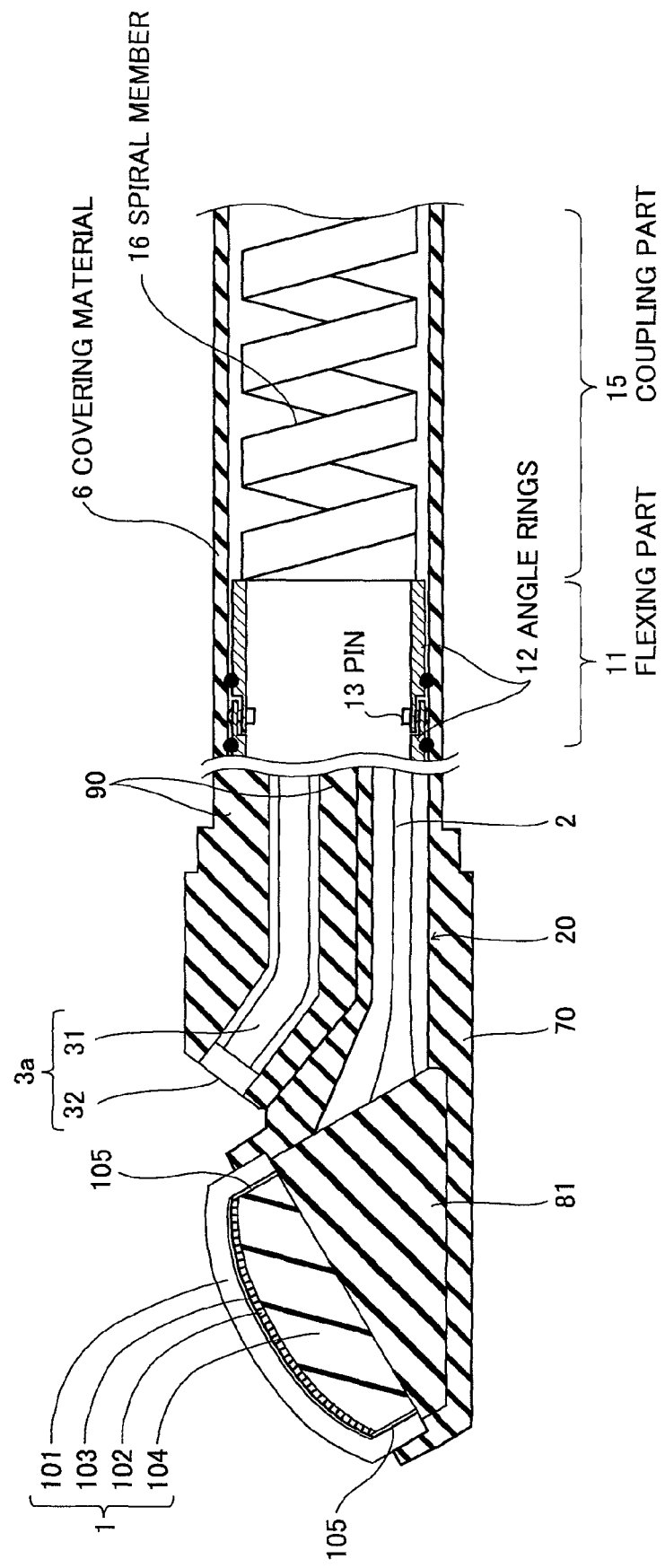
FIG. 6 is a sectional view for explanation of a configuration of an ultrasonic endoscope according to the second embodiment.

FIG. 6 is a sectional view for explanation of a configuration of an ultrasonic endoscope according to the second embodiment of the present invention, and corresponds to FIG. 3 in the first embodiment. The ultrasonic endoscope according to the embodiment has the same configuration as that of the ultrasonic endoscope according to the first embodiment except that the exterior member 70 is formed of an electrically insulating material. The exterior member 70 is made of a resin, for example, and preferably has a coefficient of thermal conductivity equal to or more than 10 W/(m·K).

Figure 12:
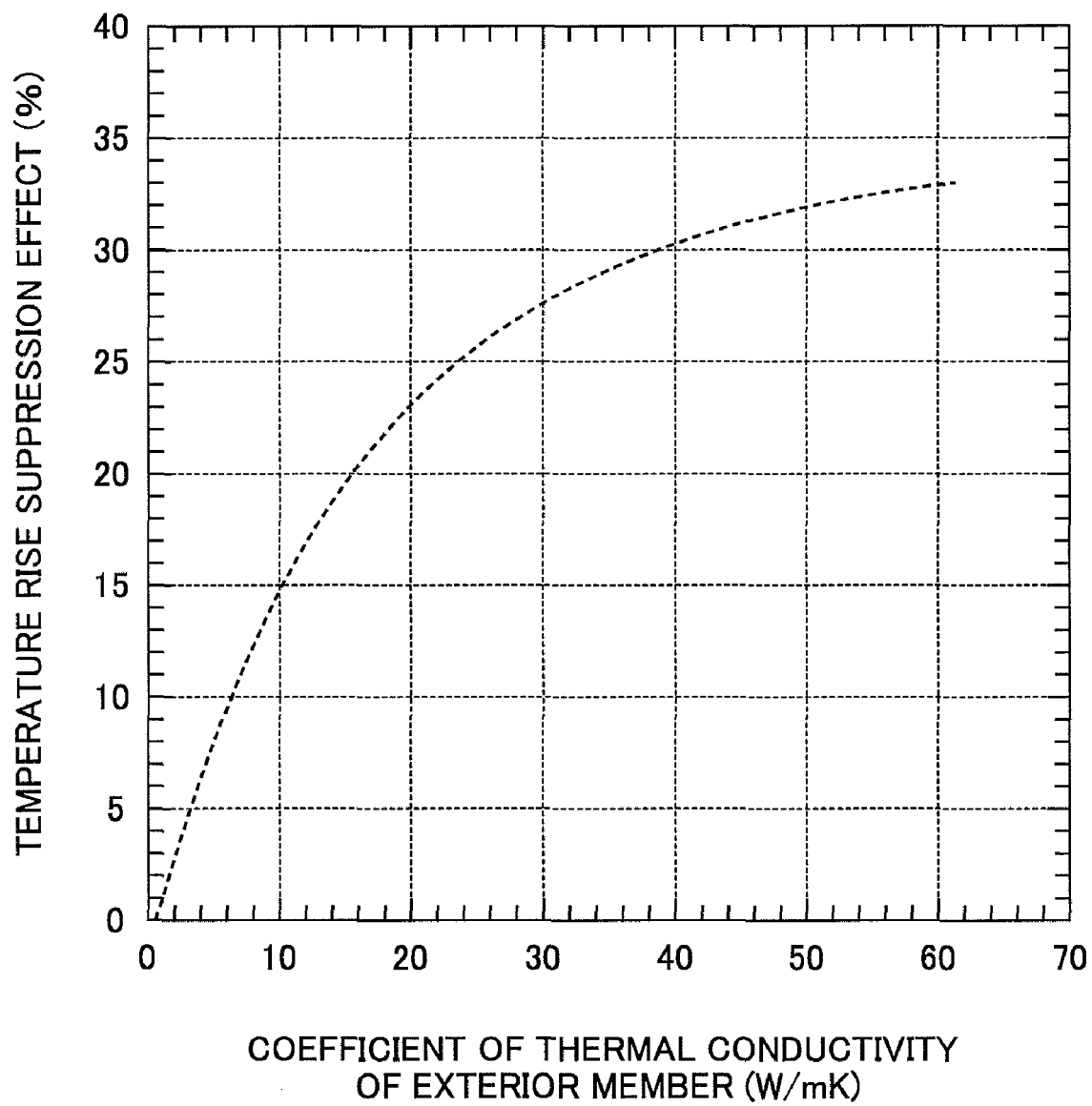
FIG. 12 is a graph showing a simulation result of a coefficient of thermal conductivity and a temperature rise suppression effect of an exterior member in the second embodiment.

FIG. 12 shows a simulation result of the coefficient of thermal conductivity and the temperature rise suppression effect of the exterior member 70 in the structure shown in the embodiment. As shown in FIG. 12, in comparison to the structure in which electrodes are provided on the lower face of the backing material, in the structure shown in the embodiment, the temperature rise of the surface of the acoustic lens 101 can be reduced by about 4% when the coefficient of thermal conductivity of the exterior member 70 is 2 W/mK, and the temperature rise of the surface of the acoustic lens 101 can be reduced by about 14% when the coefficient of thermal conductivity of the exterior member 70 is 10 W/mK.

Also according to the embodiment, the temperature rise at the leading end of the insertion part of the ultrasonic endoscope 40 can be suppressed as is the case of the first embodiment.

Figure 7:
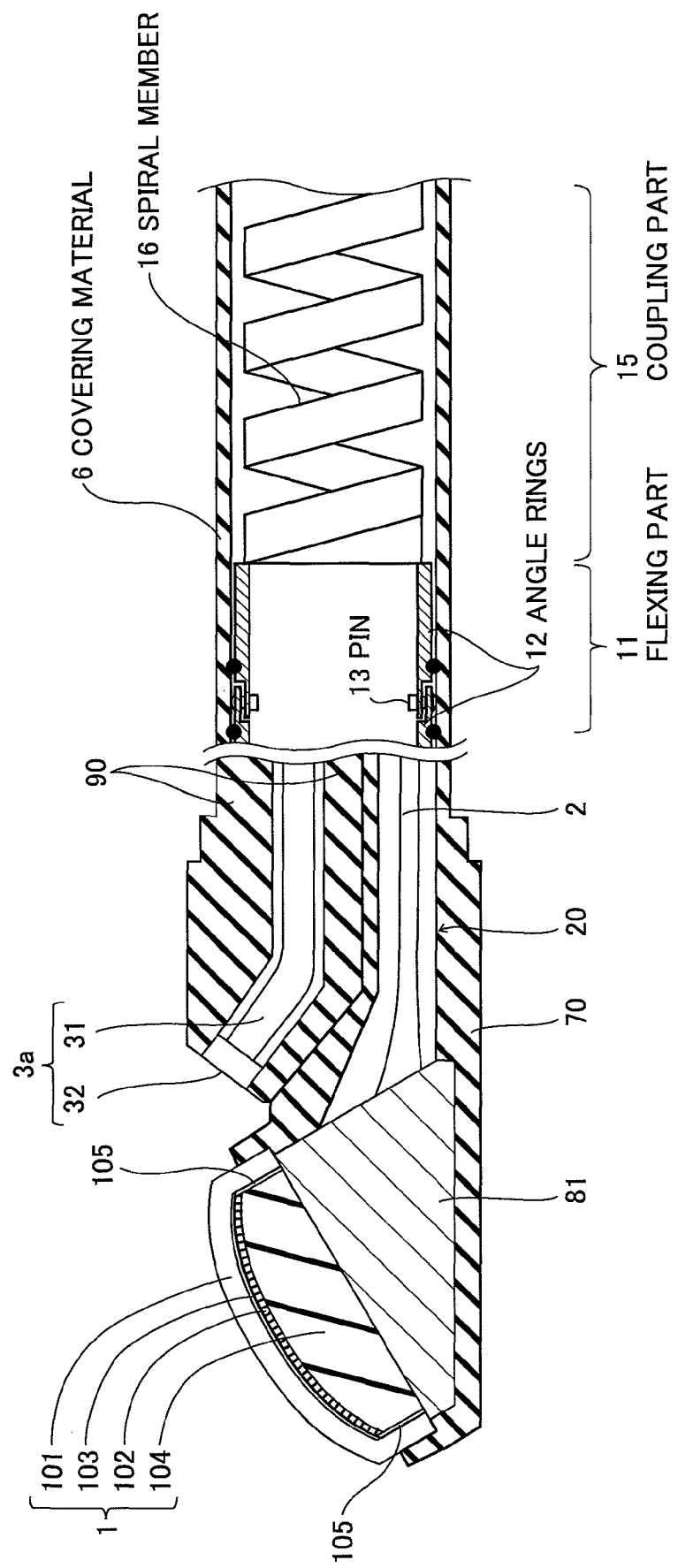
FIG. 7 is a sectional view for explanation of a configuration of an ultrasonic endoscope according to the third embodiment.

FIG. 7 is a sectional view for explanation of a configuration of an ultrasonic endoscope according to the third embodiment of the present invention, and corresponds to FIG. 3 in the first embodiment. The ultrasonic endoscope according to the embodiment has the same configuration as that of the ultrasonic endoscope according to the first embodiment except that the heat conducting member 81 is formed of an electrically conducting material (e.g., a metal including stainless steel such as SUS 304 or copper), and the exterior member 70 is formed of an electrically insulating material. The exterior member 70 is made of a resin, for example, and preferably has a coefficient of thermal conductivity equal to or more than 10 W/(m·K).

Also according to the embodiment, the temperature rise at the leading end of the insertion part of the ultrasonic endoscope 40 can be suppressed as is the case of the first embodiment.

Figure 8:
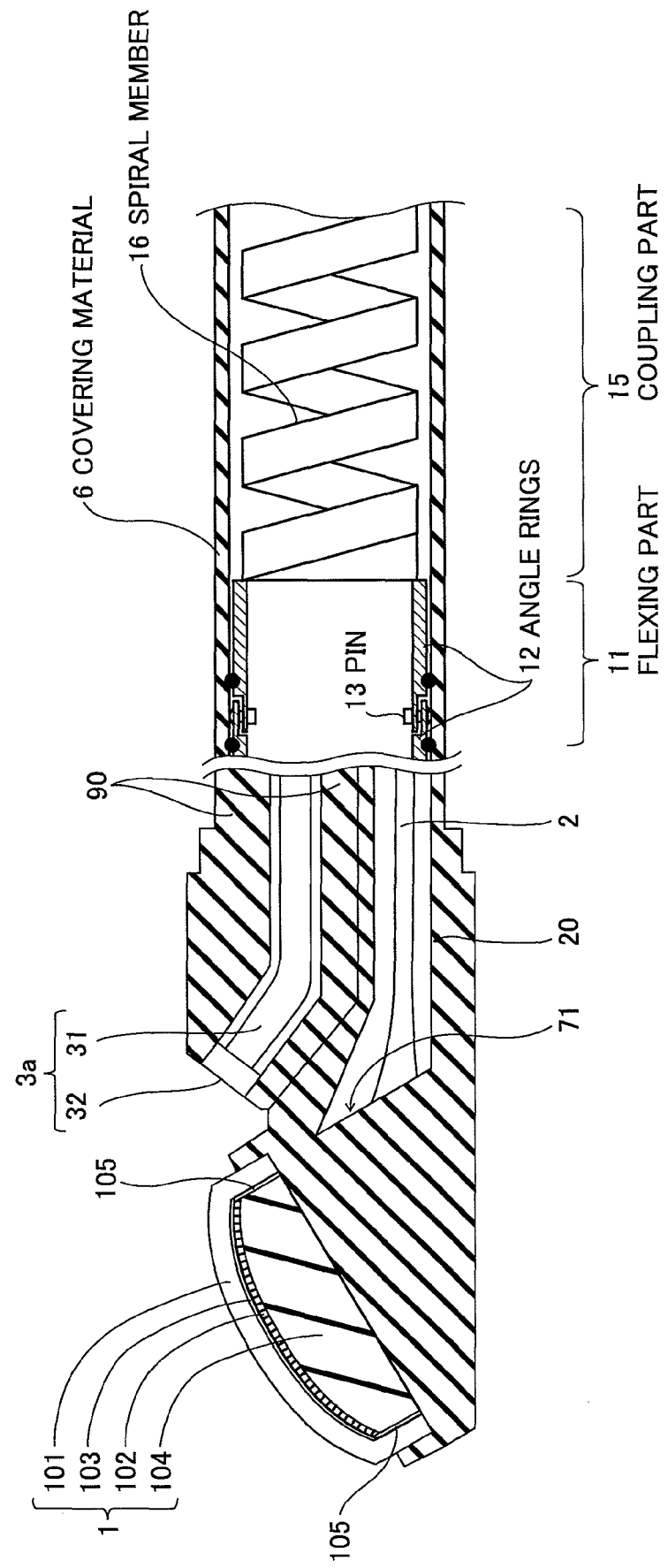
FIG. 8 is a sectional view for explanation of a configuration of an ultrasonic endoscope according to the fourth embodiment.

FIG. 8 is a sectional view for explanation of a configuration of an ultrasonic endoscope according to the fourth embodiment of the present invention, and corresponds to FIG. 6 in the second embodiment. The ultrasonic endoscope according to the embodiments the same as the second embodiment except that no heat conducting member 81 is provided, and a part of the inner surface of the exterior member 70 is convex inward and the convex portion 71 is connected to the back face of the backing material 104. The convex portion 71 and the backing material 104 are connected to each other via an adhesive having high thermal conductivity, for example.

According to the embodiment, the heat generated in the ultrasonic transducers 102 transfers to the exterior member 70 via the backing material 104, and is released from the outer surface of the exterior member 70 to the outside. Further, the heat generated in the backing material 104 also transfers to the exterior member 70 and is released from the outer surface of the exterior member 70 to the outside. Therefore, the temperature rise at the leading end of the insertion part of the ultrasonic endoscope 40 can be suppressed. Further, since the exterior member 70 is formed of an electrically insulating material, the electric insulation of the outer surface of the exterior member 70 from the ultrasonic transducer part 1 can be ensured.

Figure 9:
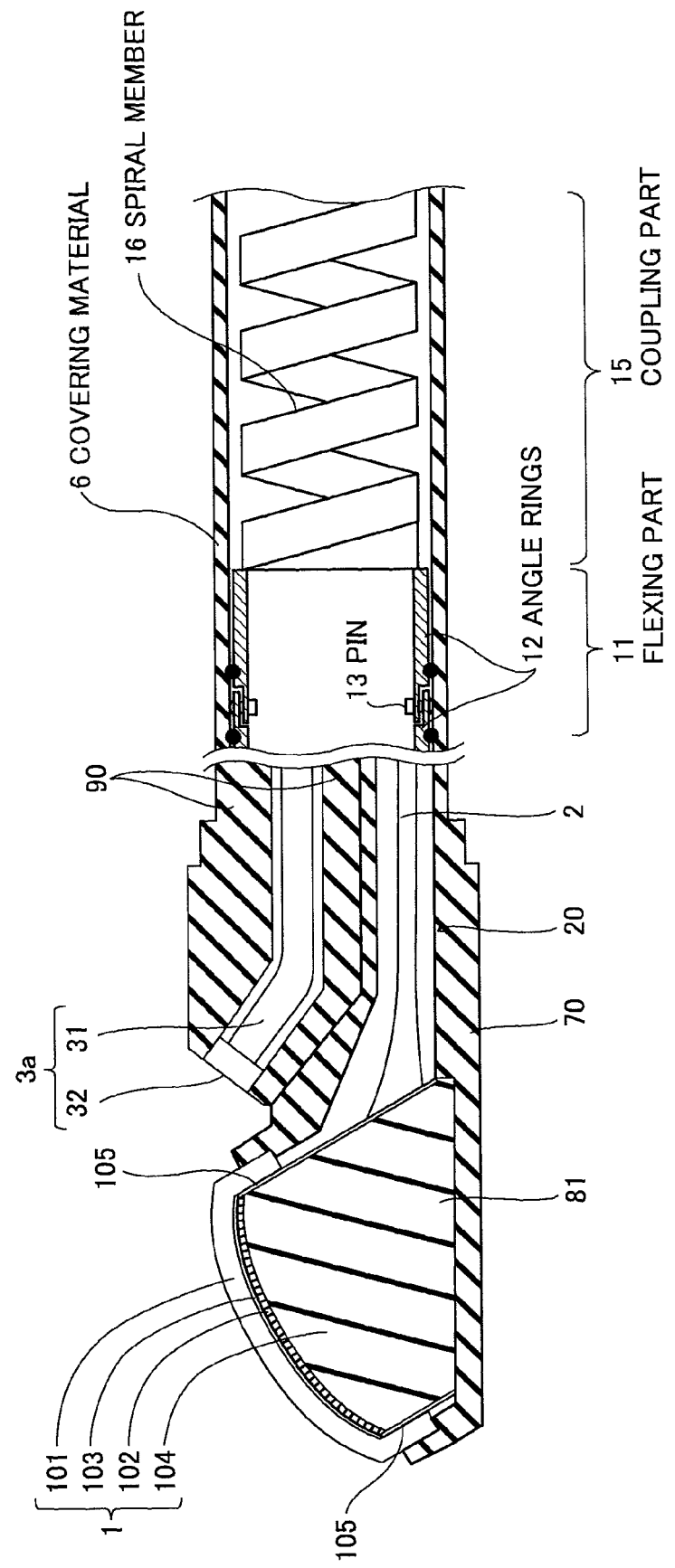
FIG. 9 is a sectional view for explanation of a configuration of an ultrasonic endoscope according to the fifth embodiment.

FIG. 9 is a sectional view for explanation of a configuration of an ultrasonic endoscope according to the fifth embodiment of the present invention, and corresponds to FIG. 6 in the second embodiment. The ultrasonic endoscope according to the embodiment is the same as the second embodiment except that no heat conducting member 81 is provided and the back face of the backing material 104 is connected to the inner surface of the exterior member 70. The exterior member 70 and the backing material 104 are connected to each other via an adhesive having high thermal conductivity, for example.

According to the embodiment, the heat generated in the ultrasonic transducers 102 transfers to the exterior member 70 via the backing material 104, and is released from the outer surface of the exterior member 70 to the outside. Further, the heat generated in the backing material 104 transfers to the exterior member 70 and is released from the outer surface of the exterior member 70 to the outside. Therefore, the temperature rise at the leading end of the insertion part of the ultrasonic endoscope 40 can be suppressed. Further, since the exterior member 70 is formed of an electrically insulating material, the electric insulation of the outer surface of the exterior member 70 from the ultrasonic transducer part 1 can be ensured.

In the above-mentioned respective embodiments, it is not necessary that the ultrasonic transducer 102 has a structure formed by stacking plural piezoelectric material layers, but may have a single piezoelectric material layer. Further, the ultrasonic endoscope may have no imaging part 3 nor light guide part 3*a* for optical observation of the object. Furthermore, in the fourth and fifth embodiments, the exterior member 70 may be formed of an electrically conducting material (e.g., stainless steel such as SUS 304).

Figure 10:
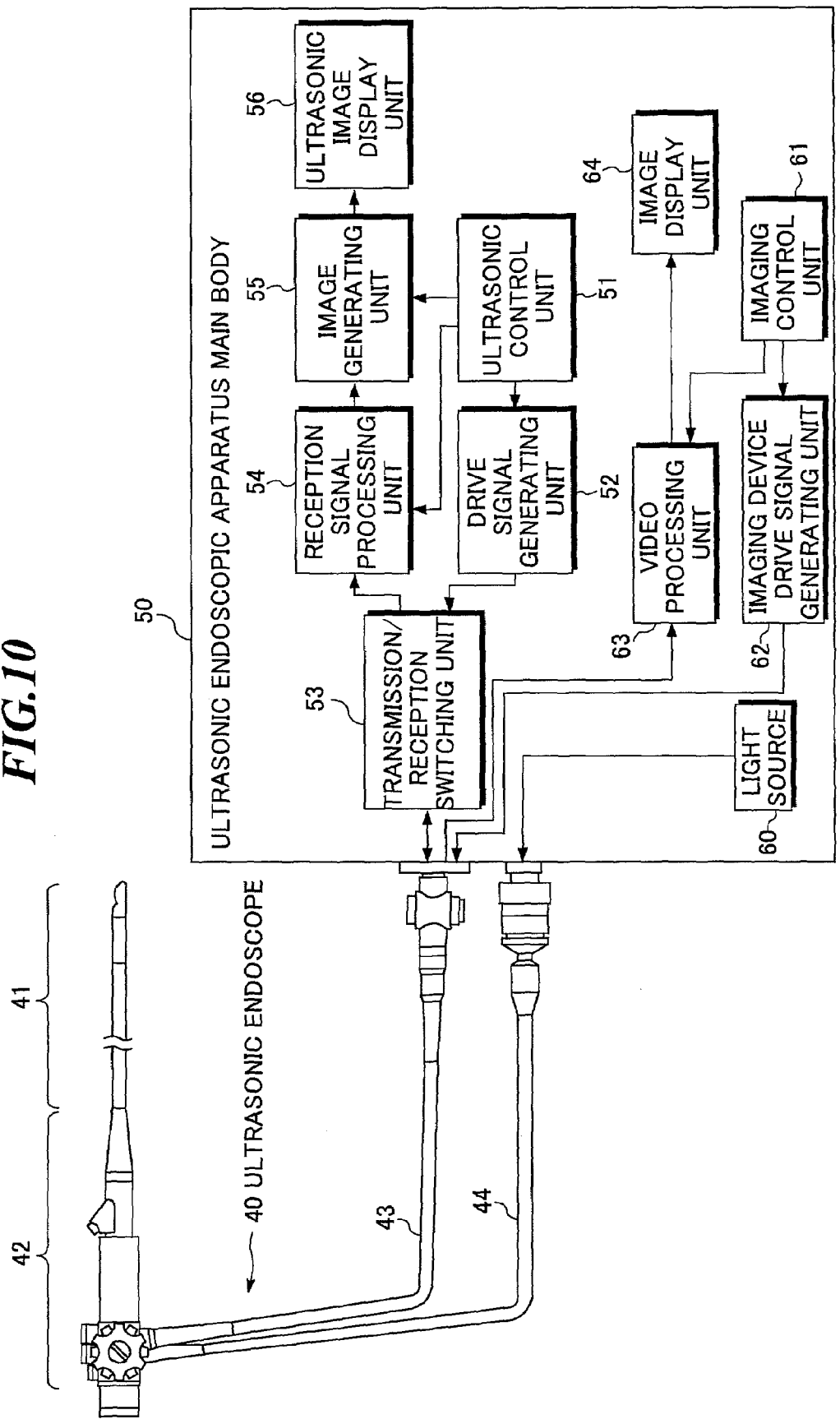
FIG. 10 shows an ultrasonic endoscopic apparatus including the ultrasonic endoscope according to the respective embodiments of the present invention and an ultrasonic endoscopic apparatus main body.

FIG. 10 shows an ultrasonic endoscopic apparatus including the ultrasonic endoscope according to the respective embodiments of the present invention and the ultrasonic endoscopic apparatus main body. The plural ultrasonic transducers included in the ultrasonic transducer part 1 (FIG. 3) are electrically connected to the ultrasonic endoscopic apparatus main body 50 by the plural shield lines via the insertion part 41, the operation part 42, and the connecting cord 43. Those shield lines transmit plural drive signals generated in the ultrasonic endoscopic apparatus main body 50 to the respective ultrasonic transducers and transmit plural reception signals outputted from the respective ultrasonic transducers to the ultrasonic endoscopic apparatus main body 50.

The ultrasonic endoscopic apparatus main body 50 includes an ultrasonic control unit 51, a drive signal generating unit 52, a transmission/reception switching unit 53, a reception signal processing unit 54, an image generating unit 55, an ultrasonic image display unit 56, a light source 60, an imaging control unit 61, an imaging device drive signal generating unit 62, a video processing unit 63, and an image display unit 64.

The ultrasonic control unit 51 controls imaging operation using the ultrasonic transducer part 1. The drive signal generating unit 52 includes plural drive circuits (pulsers or the like), for example, and generates plural drive signals to be used for respectively driving the plural ultrasonic transducers. The transmission/reception switching unit 53 switches between output of the drive signals to the ultrasonic transducer part 1 and input of the reception signals from the ultrasonic transducer part 1.

The reception signal processing unit 54 includes plural preamplifiers, plural A/D converters, a digital signal processing circuit or CPU, for example, and performs predetermined signal processing such as amplification, phase matching and addition, and detection on the reception signals outputted from the plural ultrasonic transducers. The image generating unit 55 generates image data representing ultrasonic images based on the reception signals on which the predetermined signal processing has been performed. The ultrasonic image display unit 56 displays an ultrasonic image based on the image data generated in this manner.

The light source 60 emits light to be used for illumination of the object. The light outputted from the light source 60 illuminates the object via the optical fiber 31 (FIG. 3) of the universal cord 44 through the illumination window 32 (FIG. 3) of the insertion part 41. The illuminated object is imaged by the imaging part 3 through the observation window 3*d* (FIG. 2) of the insertion part 41, and video signals outputted from the imaging part 3 are inputted to the video processing unit 63 of the ultrasonic endoscopic apparatus main body 50 via the connecting cord 43.

The imaging control unit 61 controls imaging operation using the imaging part 3. The imaging device drive signal generating unit 62 generates drive signals to be supplied to the imaging part 3. The video processing unit 63 generates image data based on the video signals inputted from the imaging part 3. The image display unit 64 inputs the image data from the video processing unit 63 and displays images of the object.

The invention claimed is:

1. An ultrasonic endoscope including an insertion part, and an operation part provided at the base end of the insertion part, said insertion part comprising:
   an elongated tube having flexibility for insertion into a body of object;
   an ultrasonic transducer part including:
   plural ultrasonic transducers;
   a backing material on a surface of which said plural ultrasonic transducers are arranged;
   at least one wiring board provided on at least one side face of said backing material and having plural electrode pads electrically connected to said plural ultrasonic transducers; and
   signal lines connected to said plural electrode pads, for transmitting signals to said plural ultrasonic transducers, respectively;
   an exterior member for accommodating said ultrasonic transducer part and having an outer surface to be contacted with the body; and
   a heat conducting part provided inside of said exterior member and respectively connected to said ultrasonic transducer part and an inner surface of said exterior member,
   wherein said heat conducting part is directly connected to a back face of said backing material, and said heat conducting part transfers a heat generated in said plural ultrasonic transducers via said backing material to said exterior member.

2. The ultrasonic endoscope according to claim 1, wherein one of said heat conducting member and said exterior member has an electric insulation property.

3. The ultrasonic endoscope according to claim 1 wherein said exterior member comprises stainless steel.

4. An ultrasonic endoscope including an insertion part, and an operation part provided at the base end of the insertion part, said insertion part comprising:
   an elongated tube having flexibility for insertion into a body of object;
   an ultrasonic transducer part including:
   plural ultrasonic transducers;
   a backing material on a surface of which said plural ultrasonic transducers are arranged;
   at least one wiring board provided on at least one side face of said backing material and having plural electrode pads electrically connected to said plural ultrasonic transducers; and
   signal lines connected to said plural electrode pads, for transmitting signals to said plural ultrasonic transducers, respectively; and
   an exterior member for accommodating said ultrasonic transducer part, having an outer surface to be contacted with the body and including a heat conducting part connected to said ultrasonic transducer part;
   wherein said heat conducting part is directly connected to a back face of said backing material, and said heat conducting part transfers a heat generated in said plural ultrasonic transducers via said backing material to said exterior member.

5. The ultrasonic endoscope according to claim 4, wherein said exterior member comprises stainless steel.

6. An ultrasonic endoscope including an insertion part, and an operation part provided at the base end of the insertion part, said insertion part comprising:
   an elongated tube having flexibility for insertion into a body of object;
   an ultrasonic transducer part including:
   plural ultrasonic transducers;
   a backing material on a surface of which said plural ultrasonic transducers are arranged;
   at least one wiring board provided on at least one side face of said backing material and having plural electrode pads electrically connected to said plural ultrasonic transducers;

signal lines connected to said plural electrode pads, for transmitting signals to said plural ultrasonic transducers, respectively; and a heat conducting part connected to an inner surface of said exterior member; and an exterior member for accommodating said ultrasonic transducer part and having an outer surface to be contacted with the body;

wherein said heat conducting part is directly connected to a back face of said backing material, and said heat conducting part transfers a heat generated in said plural ultrasonic transducers via said backing material to said exterior member.

7. The ultrasonic endoscope according to claim 6, wherein a back face of said backing material is connected to the inner surface of said exterior member.

8. The ultrasonic endoscope according to claim 6, wherein said exterior member comprises stainless steel.

* * * * *